United States Patent [19]

Noppe et al.

[11] Patent Number: 5,206,122

[45] Date of Patent: Apr. 27, 1993

[54] LIGHT STABLE PHYSICAL DEVELOPER

[75] Inventors: Marcus J. M. Noppe, Kalmthout; Lucas A. M. Van Nuffel, Merksem, both of Belgium

[73] Assignee: Janssen Pharmaceutica N.V., Beerse, Belgium

[21] Appl. No.: 662,586

[22] Filed: Feb. 28, 1991

[30] Foreign Application Priority Data

Mar. 14, 1990 [GB] United Kingdom ............... 9005753

[51] Int. Cl.$^5$ .............................................. G03C 5/24
[52] U.S. Cl. ................................... 430/414; 430/413; 430/417; 430/424; 430/477
[58] Field of Search ............... 430/413, 414, 417, 424, 430/477

[56] References Cited

U.S. PATENT DOCUMENTS

| | | | |
|---|---|---|---|
| 2,131,742 | 10/1938 | Kumetat et al. | 430/424 |
| 2,132,169 | 10/1938 | Kumetat et al. | 430/424 |
| 2,172,192 | 9/1939 | Dieterle et al. | 430/424 |
| 3,647,439 | 3/1972 | Bass | 439/477 |
| 3,859,092 | 1/1975 | Gysling et al. | 430/417 |
| 3,860,500 | 1/1975 | Gysling | 430/417 |
| 3,860,501 | 1/1975 | Gysling | 430/417 |
| 4,095,981 | 6/1978 | Goffe et al. | 430/417 |

*Primary Examiner*—Hoa Van Le

[57] ABSTRACT

A light-stable physical developer comprising a solution of silver ions, a desensitizing agent and a reducing agent. A method for the detection of one or more components of an aggregate formed between at least one specific binding agent and its corresponding bindable substance by labelling at least one component of said aggregate with a marker and contacting said aggregate with said light-stable physical developer, whereby under influence of the marker a metal particle is formed which can be detected. Further the invention also relates to products, e.g. a test-kit adapted for carrying out the above mentioned method.

6 Claims, No Drawings

LIGHT STABLE PHYSICAL DEVELOPER

BACKGROUND OF THE INVENTION

During the last years, methods have been introduced wherein aggregates formed between specific binding agents and bindable substances are detected by labelling said aggregates directly or indirectly with small size metal particles, particularly gold particles. Depending on the circumstances, these particles can be detected, e.g. by direct visual examination, by microscopic or spectrophotometric techniques. A description of the "immunogold staining (IGS) technique", "the sol particle immuno assay (SPIA) technique" or specific applications and improvements thereof can be found in U.S. Pat. Nos. 4,313,734, 4,446,238, 4,420,558, EP-A-0,165,633, EP-A-0,165,634, EP-A-0,158,746, EP-A-0,293,947 and in IBRO handbook series, Wiley, New York, 1983, pages 347 to 372.

Starting from a relatively unknown method for labelling cell surface antigens, metal particles have today become widely used in a variety of detection and/or quantitive determination problems. The possibility of direct visual examination of metal particles and the advantage that the signal generated is permanent and not prone to rapid degradation makes it an interesting marker for simple and rapid assays. Moreover metal markers, preferably gold markers, seem preferable over radioisotope markers due to the very low health hazard related to working with the former.

Next it was found that the signal of a metal marker such as colloidal gold can be augmented significantly by subjecting the colloidal gold markers to a so-called physical enhancement procedure. The effect of such a physical enhancement procedure is that the typical reddish optical gold signal turns into a deep-brown to black silver signal having a much higher intensity. In said procedure, the metal markers used as a label catalyze the reduction of silver ions present in the developing solution. The latter results in a specific deposition of a metallic silver layer at the metal particle site. The thus formed metallic silver particles in turn catalyze the reduction of more silver ions from the physical developing solution, creating an autocatalytic process.

Art-known physical developing solutions generally consist of a solution containing a soluble metal salt such as silver nitrate, a reducing agent such as hydroquinone, an appropriate buffer and optionally a complexant to tie up the metal ions and make them less susceptible to reduction.

Although the use of these art-known physical developers results in an augmented signal, there are a number of drawbacks associated with it. Indeed, it is well known that silver ions may form light sensitive salts such as silver bromide and silver chloride which are readily reduced to metallic silver under the influence of light, starting an autocatalytic process. This non-specific process of self-nucleation contributes to the occurence of background to a significant extent. It may be disturbingly strong under conditions of intense light, e.g. in the monitoring of test samples under a light microscope, or also when the physical development process is slow and the test sample is exposed to light for a prolonged time.

Consequently, the aim of the present invention is to provide a sensitive and practicable physical developer for use in a variety of metal based assays which is light-stable and does not give rise to undesired non-specific deposition of metal particles.

The present invention relates to a physical developer comprising an aqueous solution of silver ions, a reducing agent, a desensitizing agent and, if desired, a buffer system and one or more adjuvants.

Further there is provided a method for qualitatively and/or quantitatively determining one or more components of an aggregate formed between at least one specific binding agent and its corresponding bindable substance, which comprises labelling at least one component of said aggregate with a marker and contacting said aggregate with a physical developer whereby under influence of the marker a silver particle is formed which can be determined qualitatively, characterized in that the physical developer is a physical developer according to the present invention, comprising a solution of silver ions, a desensitizing agent and a reducing agent.

Another aspect of the present invention is to provide versatile products such as test-kits adapted for carrying out the above mentioned methods.

In the present invention the light-sensitivity of the traditional physical developers based on silver ions is counteracted by adding a desensitizing agent to the developer. Preferred desensitizing agents for use in the present invention are electron acceptors such as, 6-ethoxy-1-methyl-2-(3-nitrostyryl)quinolinium methyl sulfonate known as Pinakryptol Yellow ® and the like desensitizing agents.

The reducing agents for use in the present physical developer include any agents which reduce silver ions from a physical developer in proximity of an active site. Preferably said reducing agents form stable solutions with the constituents of the improved physical developer. As a reducing agent there may particularly be mentioned, 1,2-dihydroxybenzene, 1,4-dihydroxybenzene (Hydroquinone), 4-methylaminophenolsulfate (Metol ®), 4-aminophenol, 1,4-diaminobenzene, 1,2-diaminobenzene, N-(4-hydroxyphenyl)glycine, 2,4-diaminophenol, 1-phenyl-3-hydroxypyrazole (Phenidone ®) or mixtures thereof. As other adjuvants for the improved physical developer there may be mentioned, buffers, preservatives, e.g., anti-oxidants or organic stabilizers, speed regulators, bactericides and the like, such as, for example, sodium sulfite, sodium bisulfite, sodium citrate and the like.

Suitable pH adjusting agents are for example, acetic acid, citric acid, sodium hydroxide or a salt of any of these or a buffer system based on tris(hydroxymethyl)aminomethane. The pH of the physical developer preferably ranges from about 5 to 9, in particular from about 6 to 8. In general the pH of the physical developer is limited to the range wherein the specific binding agent and the corresponding bindable substance are stable.

Apart from the silver ions, the reductant and desensitizing agent, the preferred physical developing solution also comprises an excess of a complexant to tie up the metal ions and to make them less susceptible for reduction. Favourable complexants for use in the present invention are described in EP-A-0,293,947 and include pyridine, aminopyridine, nicotinamide, quinoline, imidazole, histidine, benzimidazole, pyrazole, purine and the like aromatic heterocyclic ring systems.

An exemplary mode of preparing the physical developer of this invention comprises dissolving or suspending the desensitizing agent in an aqueous solution comprising silver ions, reductant, buffer and any adjuvants.

In the final solution, the ratio of desensitizing agent:silver ions is from about 50 g/mol to 0.5 g/mol silver ions, in particular from about 50 g/mol to 5 g/mol silver ions, or from 35 g/mol to 15 g/mol silver ions. The concentration of silver ions ranges from 0.001 mol/l to 0.1 mol/l in particular from about 0.005 mol/l to 0.5 mol/l, or from 0.07 mol/l to 0.3 mol/l.

In a preferred embodiment the physical developer is prepared by mixing two stable and liquid solutions. One solution, hereinafter being referred to as enhancer, comprises silver ions, a desensitizing agent, a molar excess of complexant with respect to the silver ions and optionally a buffer system. In particular the molar excess of complexant versus the silver ions ranges from about a two to a twohunderd-fold molar excess, preferably from about a twenty to a hunderd-fold molar excess. The other solution, hereinafter being referred to as initiator, comprises a reducing agent and optionally a buffer system and an anti-oxidant and/or organic stabilizer, such as, for example, sodium sulfite, sodium bisulfite and the like. Preferably the dilution of both the enhancer and the initiator are such that mixing an equal volume of each solution will yield a light-stable physical developer as described hereinabove. In some instances the enhancer and initiator may be prepared from their corresponding dry constituents by adding an appropriate amount of water. In order to facilitate the preparation of the enhancer and/or physical developer it may be appropriate to dissolve the desensitizing agent first in a small amount of an organic solvent such as N,N-dimethylformamide, N,N-dimethylacetamide and the like and to mix to thus obtained organic solution with the aqueous solution comprising the silver ions. The pH of the enhancer should be in the range from about 5 to 9, preferably from about 6.5 to 8.5. The pH of the initiator should be in the range from 2 to 7, preferably from about 3.5 to 5.5.

Although the use of desensitizing agents like Pinakryptol Yellow ® in silver halide emulsions is known, it is surprising that Pinakryptol Yellow ® can selectively prevent non-specific self-nucleation in a physical developing solution and form a light stable aqueous solution, while not adversely affecting the rate of metal deposition on the marker. Thus the present invention provides a severalfold increase in the ratio between marker-specific reduction rate and rate of self-nucleation. A noteworthy consequence thereof is that the present physical developer can react to the maximum, i.e. until depletion of all silver ions, whereafter both marker specific development and self-nucleation—if any—sharply decrease and stop. This makes the physical developing procedure less dependent on external and procedural parameters. More in particular this means that one does not any longer need to time the development process in order to stop it when background noise by non-specific metal deposition starts. With the compositions of the present invention the development process may run to completion and therefore be left unmonitored.

The increased ratio between marker-specific reduction rate and rate of non-specific self-nucleation can be exploited in several ways. The sensitivity can be increased by keeping the marker longer into contact with the physical developer, or the speed of the marker-specific development can be increased and this without loosing the flexibility offered by a safe period of time between the moment of optimum marker development and the moment where self-nucleation starts to give an increased background. In some cases a combination of both increased overall speed and sensitivity can be implemented. The speed and sensitivity can be modulated by changing the concentration and the nature of the silver ions, in particular their ligands, the desensitizing agent, the reducing agent and/or the pH of the developing solution. For example, increasing the concentration of the silver ions and/or increasing the pH and/or using a stronger reducing agent will result in a faster developing procedure. Conversely, the developing procedure can be slowed down by lowering the concentration of silver ions and/or lowering the pH and/or by employing a weaker reducing agent. The speed, especially with markers smaller than 5 nm, can perfectly be modulated from very fast (10-20 sec) to slow (30 min or more). Preferably the developing time is modulated from about 10 seconds to two minutes, in particular from 10 seconds to one minute.

The above described physical developers are preferably employed in methods for qualitatively and/or quantitatively determining one or more components of an aggregate formed between at least one specific binding agent and its corresponding bindable substance whereby at least one component of said aggregate is labelled with a metal marker which catalyzes directly or indirectly the reduction of silver ions from a physical developer.

The marker for use in the method according to the invention defines any particle which can catalyze the reduction of metal ions, resulting in a deposition of the corresponding metal particles at the site of the said marker.

Said markers comprise metals, metal compounds or polymers optionally coated or impregnated with metals or metal compounds which can catalyze directly or indirectly the reduction of metal ions on their surface. As examples of such metals there may be named gold, silver, thallium, platinum, palladium as well as copper, nickel and the like with gold being preferred. As examples of metal compounds there may be named their corresponding complexes or chelates and sulfides. Polymers coated or impregnated with metals or metal compounds have similar properties as the metal or metal compounds but size, density and metal content can be optimally combined. For use in the preferred method the marker should be selected so that specific binding agents or their corresponding bindable substances can be attached to the marker, without loss of their affinity for their counterpart.

Particularly preferred markers for use in the method according to the present invention are either (i) colloidal metal particles, optionally a sol containing metals or metal sulfides; or (ii) metal chelates, especially those incorporating ethylenediaminotetraacetic acid (EDTA) or diethylenetriaminepentaacetic acid (DTPA) groups; or (iii) polymers optionally impregnated with metals or metal sulfides, e.g., polymerization products of benzidine derivatives such as, for example diaminobenzidine polymers.

Said preferred method can conveniently be carried out by immobilizing the specific binding agent or the corresponding bindable substance, directly or indirectly, on a solid support, contacting the support with a counterpart labelled with a marker which catalyzes the reduction of the metal ions of the physical developer, and adding the physical developer before or after the separation of the bound and free labelled components, whereby during the reaction or after an adequate reaction time, the formed metal particles are quantitatively and/or qualitatively determined in the test sample and/or in the derived fractions to provide a qualitative and/or quantitative indication of the component or components to be determined. In some instances it may be preferable to contact the support containing the immobilized bindable substance with a first binding agent specific to said bindable substance to form an aggregate herewith, and subsequently contacting the support carrying the thus formed aggregate with a second binding protein, which is specific to the said first binding protein, labelled with marker. The thus described method is particularly suited for the determination of immunochemical components, such as haptens, antigens and antibodies.

Further, the present invention may also be employed for quantitatively and/or qualitatively determining an acceptor substance, such as a protein or a nucleic acid, which is directly immobilized on a solid support and bound with the aforementioned marker.

The determinations to be made according to the preferred method of this invention may be performed homogeneously or heterogeneously. Homogeneous determinations are particularly simple to perform but require a measurable change of the perceived signal arising from either those markers present in the labelled reagent or in the labelled aggregate formed between the labelled reagent and the particles to be determined. In those instances where no such distinction is possible, heterogeneous determinations will have to be performed.

Homogeneous determinations are advantageous due to the fact that it is not necessary to physically separate the bound and unbound labelled species, thus reducing the number of steps necessary to perform an assay. The reaction between the labelled component and the corresponding binding counterpart causes the measurable change in the label's participation in or modulation of the signal generating moiety necessary to perform a homogeneous determination. The distribution of the markers between the bound and unbound species may be differentiated by the inability or altered ability of the said markers to affect the signal arising therefrom after development when present in the bound species.

A homogeneous determination may conveniently be performed according to art-known procedures such as, for example, the competitive binding technique. The sample containing the analyte is combined with a binding counterpart of the analyte, a labelled reagent comprising a marker coupled to the analyte or a specific binding analogue thereof, and the physical developer necessary to convert the marker to the signal generating moiety itself. Alternatively, a sequential determination may be performed whereby the sample and the analyte binding counterpart are first combined and thereafter the detectant reagent added.

In many instances it is not possible to perform homogeneous determinations. In these cases a heterogeneous determination can be a particularly attractive alternative. In general, the heterogeneous determination system comprises at least two basic constituents and the physical developer which are combined simultaneously or subsequently, i.e. the analyte to be detected, a binding counterpart labelled with a marker and the physical developer necessary to convert the marker to the signal generating moiety itself. If necessary after an appropriate incubation period or periods the labelled reagent becomes bound to the corresponding bindable substance to be detected whereby the ratio of the bound species to the unbound species is a function of the amount of analyte being present. The bound and unbound species are physically separated and the amount of label being present in one thereof is determined.

Various means of performing the separation step and of performing the binding reactions are known in the art. The said separation may involve conventional techniques such as, for example, by employing a solid-phase antibody or antigen, a second antibody, or a solid-phase second antibody; or by the use of immuno complex precipitation agents, adsorbents, and the like. The said binding reactions may for example include the so-called competitive binding technique, the sequential saturation technique, the sandwich technique, and the like.

The preferred determinations to be made according to the method of this invention are heterogeneous determinations which are generally based on the principle that the labelled aggregate formed between the specific binding protein and the bindable substances is at some time immobilized in such manner that any unreacted particles can be washed off, whereupon the immobilized particles are detected "in situ" or, if desired, after disengagement in any other phase derived therefrom.

In a particularly preferred embodiment, the binding substance to be detected, which may be contained in a crude test specimen or in a purified or partly purified fraction derived therefrom, is immobilized on an appropriate immobilizing support prior to its complexing with the labelled binding agent, specific to said bindable substance.

The immobilization of the bindable substance may be carried out following the usual techniques, e.g., by spotting an aliquot of the test specimen on the immobilizing support or by immersing the latter in the test sample and subsequently drying and optionally washing off non-immobilized material. This is the so-called direct technique. As immobilizing supports for this technique use can be made of various materials, in general polymeric materials like, nitrocellulose, diazobenzyloxymethyl (DBH)- and diazophenylthioether (DPT) modified cellulose paper, paper, paper or cellulose acetate activated with cyanogen bromide, agarose, nylon, plastics and the like, which may take any form which is convenient for the determination process, e.g. sheets, beads, welled plates, dip-sticks and the like.

The support is then brought into contact with a labelled binding agent under conditions which allow aggregate formation between the binding agent and the corresponding bindable substances. Consequently, at the sites where the bindable substance is immobilized, markers will be immobilized in turn in amounts proportional to the concentration of the immobilized bindable substance.

In a variant of this method, the immobilized bindable substance is first allowed to react with a first binding agent which is specific therefore and subsequently the thus immobilized phase is brought into contact with the markers attached to a second binding agent which is specific for said first binding agent.

Because of the lack of selectivity and specificity of the immobilizing process as described above, the direct method is usually employed with relatively pure or purified test samples or fractions. For more complex samples, the direct method will often be less suitable, as the non-specific immobilization of a large excess of non-desired material will interfere with the sensitivity and specificity of the determination.

To avoid this problem, which is important with regard to routine analyses, an indirect or so-called sandwich technique can be used. In this technique, a purified or enriched primary specific binding agent is immobilized on a solid support. The latter is contacted with the test sample under conditions which allow the complexing of the corresponding bindable substances, which consequently become immobilized themselves. After removal of the test sample and washing of the support, the latter is contacted with a suspension of markers coated with secondary specific binding agents which are able to bind to uncomplexed sites of the immobilized bindable substance.

The most straightforward case of embodiment to which the invention is applicable is a flow-through environment consisting of bindable substance which is immobilized, directly or indirectly, to a solid phase, and a liquid phase mobile relative to the solid phase. Depending on the direction of the liquid phase flow versus the solid phase, this solid phase can be liquid-permeable or -unpermeable. For example, a permeable membrane can be used as solid phase, allowing for a perpendicular flow of the liquid phase through that membrane. On the other hand, an unpermeable solid phase can be used in combination with a lateral liquid flow.

During the first step of the embodiment, the liquid phase containing the marked specific binding agent is brought into contact with the bindable substance immobilized on the solid phase. The movement of this liquid phase relative to the solid phase may be continuous or discontinuous and must be such that the contact time between both phases allows for binding between the immobilized bindable substance and the marked specific binding agent to take place. However, this binding process not necessarily needs to reach its saturation point. The pressure drop between source and destination of the liquid phase, creating its flow, may be built in several ways. In the case of a permeable membrane as solid phase, a perpendicular flow may be created by bringing one side of this membrane into contact with a fluid-absorbing material and by applying the liquid phase on the other side. In the case of a non-permeable solid phase, a lateral flow of the liquid phase may be created by a pump.

For the second step an improved physical developer according to this invention is applied as the liquid phase. In order to maximize the ratio between marker-specific reduction speed and the speed of self-nucleation, it may be appropriate to keep both components of the physical developer, initiator and enhancer, apart until immediately before use. However, it should be emphasized that in comparison with the prior-art, stable solutions of the physical developer can be made by mixing the initiator and enhancer. In some instances it may be preferable to apply the enhancer and initiator subsequently and thus forming the improved physical developer "in situ". In view of the above considerations the physical developer of the present invention can easily be optimized towards the marker used, the sensitivity required and the contact time between the solid phase and the liquid physical developer.

In the preferred flow-through embodiment, the mixing of the two stable liquid components and the application of the resulting improved physical developer should be combined into a single action. The application of the flowing protected physical developer has a dual effect. Initially, the liquid will wash away from the solid phase all remaining marked specific binding agents which were not or only loosely bound during the first step. Because the physical development of the marker is a gradually progressive process, this material will be washed from the solid phase before any signal becomes apparent. The remaining, bound marked specific binding agents will generate a visible signal during the further contact with the protected physical developer. The flow and volume of the developer applied to the solid phase can be chosen to ensure that the contact time is long enough for an optimal detection of the immobilized marked compounds and short enough to avoid non-specific reduction at the solid phase caused by self-nucleation. Typically, these times can be modulated from a few seconds to several minutes.

The detection of the formed metal particles in a certain phase of the reaction mixture may take place using numerous techniques which are in themselves known. Said techniques are based upon the amount and/or the physical properties of the metal particles formed, preferably on the scattering and adsorption of the metal particles. As examples of these techniques there may be cited the spectrophotometric techniques such as densitometry, which will be preferred when quantitative determinations are desired. However, in view of the high sensitivity obtained the particles can easily be observed visually, optionally using a microscope.

The specific binding agents which can be employed in the preferred method according to the invention can be of various nature but will in many instances be antibodies to specified antigens or haptens. As an example of specific binding substances other than antibodies there can be mentioned phages, which are optionally chemically or genetically adapted to bind molecular or cellular materials, lectins, which specifically bind glycoproteins, *Staphylococcus aureus* protein A which specifically binds immunoglobulins of various animal species and DNA or RNA probes for gene identification. In general any other molecular interaction of sufficient specificity and affinity can be employed. Antibodies may be polyclonal or monoclonal.

In view of their general nature, the methods according to the invention have an extremely wide field of application. In principle they can be applied to the qualitative and/or quantitative determination of any substance which can be labelled with the aforementioned marker. For example, such substances comprise but are not limited to cell surface and tissue antigens, biological substances excreted by or derived from living organisms, particularly biological substances occurring in biological fluids such as saliva, lymph, blood and its derived fractions such as, plasma and serum, urine, cerebrospinal fluid, amnion fluid, and the like. Substances which can be detected include, proteins, polypeptides, peptides, like enzymes, hormones, structural proteins, nucleic acids, vitamins, polysaccharides, toxins, alkaloids, glycoproteins, haptens, metabolites, pharmacological agents, pesticides, pollutants, steroids, and any other molecule for which a specific binding counterpart exists in biological systems or can be synthesized.

Representative protein analytes include the classes of protamines, mucoproteins, glycoproteins, globulins, albumins, scleroproteins, phosphoproteins, histones, lipoproteins, chromoproteins, and nucleoproteins. Examples of specific proteins are prealbumin, $\alpha_1$-lipoprotein, human serum albumin, $\alpha_1$-acid glycoprotein, $\alpha_1$-antitrypsin, $\alpha_1$-glycoprotein, transcortin, thyroxine binding globulin, haptoglobin, hemoglobin, myoglobin, ceruloplasmin, $\alpha_2$-lipoprotein, $\alpha_2$-macroglobulin, $\beta$-lipoprotein, erythropoietin, transferin, hemopexin, fibrinogen, the immunoglobulins such as IgG, IgM, IgA, IgD, and IgE, IgG being preferred and their fragments, e.g., $F_c$, $F_{ab}$ and $F(ab)^2$ complement factors, prolactin, blood clotting factors such as fibrinogen, thrombin and so forth, insulin, melanotropin, somatotropin, thyrotropin, follicle stimulating hormone, luteinizing hormone, gonadotropin, thyroid stimulating hormone, placental lactogen, intrinsic factor, transcobalamin, serum enzymes such as alkaline phosphatase, lactic dehydrogenase, amylase, lipase, phosphatases, cholinesterase, glutamic oxaloacetic transaminase, glutamic pyruvic transaminase, and uropepsin, endorphins, enkephalins, protamine, tissue antigens, bacterial antigens, and viral antigens such as hepatitis associated antigens (e.g., $HB_sAg$, $HB_cAg$ and $HB_eAg$).

Representative hapten analytes include the general classes of drugs, metabolites, hormones, pesticides, pollutants, vitamins, and the like organic compounds. Haptenic hormones include thyroxine and triiodothyronine. Vitamins include vitamins A, B, e.g. $B_{12}$, C, D, E and K, folic acid and thiamine. Drugs include antibiotics such as aminoglycosides, e.g., gentamicin, tobramycin, amidacin, sisomicin, kanamycin, and netilmicin, penicillin, tetracycline, terramycin, chloromycetin, and actinomycetin; nucleosides and nucleotides such as adenosine diphosphate (ADP) adenosine triphosphate (ATP), flavin mononucleotide (FMN), nicotinamide adenine dinucleotide (NAD) and its phosphate derivative (NADP), thymidine, guanosine and adenosine; prostaglandins; steroids such as the oestrogens, e.g., oestriol and oestradiol, steroids; and others such as phenobarbital, phenytoin, pirimidone, ethosuximide, carbamazepine, valproate, theophylline, caffeine, propranolol, procainamide, quinidine, amitryptiline, cortisol, desipramine, disopyramide, doxepin, doxorubicin, nortryptiline, methotrexate, imipramine, lidocaine, N-acetyl-procainamide, amphetamines, catecholamines, and antihistamines. Further cardiac glycosides, and derivatives of benzodiazepine, benzimidazole, piperidine, piperazine, imidazole, triazole, pyridazine, 1,2,4-triazinedione or 2,3,5,6-tetrahydroimidazo[2,1-b]thiazoles, or amides, hydratropic acid derivatives or trialkylamines. Benzimidazole haptens comprise thiabendazole, fuberidazole, ciclobendazole, oxibendazole, parbendazole, cambendazole, mebendazole, fenbendazole, flubendazole, albendazole, oxfendazole, nocodazole and astemizole. Piperidine haptens comprise diphenoxylate, phenoperidine, haloperidol, haloperidol decanoate, bromperidol decanoate, bromperidol, moperone, trifluperidol, pipamperone, piritramide, fentanyl, benperidol, droperidol, benzitramide, benzetimide, domperidone, sufentanil, carfentanil, alfentanil, dexetimide, milenperone, difenoxin, fluspirilene, penfluridol, pimozide, lorcainide, loperamide, astemizole, ketanserine, levocabastine, cisapride, altanserin, ritanserin, 3-[2-[4-(4-fluorobenzoyl)-1-piperidinyl]ethyl]-2,7-dimethyl-4$\underline{H}$-pyrido-[1,2-a]-pyrimidin-4-one, 3-[2-[4-[bis(4-fluorophenyl)methylene]-1-piperidinyl]ethyl]-2-methyl-4$\underline{H}$-pyrido[1,2-a]pyrimidin-4-one and 3-[2-[4-[[3-(2-furanyl-methyl)-3H-imidazo[4,5-b]pyridin-2-yl]amino]-1-piperdinyl]ethyl]-2-methyl-4$\underline{H}$-pyrido[1,2-a]pyrimidin-4-one. Piperazine haptens include azaperone, fluanisone, lidoflazine, flunarizine, mianserine, oxatomide, mioflazine, clocinizine and cinnarizine. Examples of imidazole haptens are metronidazole, ornidazole, ipronidazole, tinidazole, isoconazole, nimorazole, miconazole, burimamide, metiamide, metomidate, enilconazole or imazalil, etomidate, econazole, clotrimazole, carnidazole, cimetidine, doconazole, sulconazole, parconazole, orconazole, butoconazole, triadiminole, tioconazole, valconazole, fluotrimazole, ketoconazole, oxiconazole, lombazole, bifonazole, oxmetidine, fenticonazole, fluconazole, tubulazole and (Z)-1-[2-chloro-2-(2,4-dichlorophenyl)ethenyl]-1$\underline{H}$-imidazole. Triazole haptens comprise virazole, azaconazole, etaconazole, propiconazole, penconazole, itraconazole and terconazole. Pyridazine haptens comprise for example, 3-chloro-6-[3,6-dihydro-4-(3-methylphenyl)-1(2$\underline{H}$)-pyridazine, 3-methoxy-6-[4-(3-methylphenyl)-1-piperazinyl]pyridazine and the compounds of Publ. Eur. Pat. Appl. No. 0,156,433. 1,2,4-Triazinediones comprise for example, 2-chloro-$\alpha$-(4-chlorophenyl)-4-(4,5-dihydro-3,5-dioxo-1,2,4-triazin-2(3$\underline{H}$)-yl)benzeneacetonitrile, 2,6-dichloro-$\alpha$-(4-chlorophenyl)-4-(4,5-dihydro-3,5-dioxo-1,2,4-triazin-2(3$\underline{H}$)-yl)benzeneacetonitrile and the compounds of Publ. Eur. Pat. Appl. No. 0,170,316. Trialkylamines are, for example, diisopromine, prozapine. 2,3,5,6-Tetrahydroimidazo[2,1-b]thiazoles comprise, for example, tetramisole or levamisole.

Amides comprise for example, closantel, ambucetamide, isopropamide, buzepide metiodide, dextromoramide. A hydratropic acid hapten is, for example, suprofen.

The purposes of the determinations can be multiple. In certain applications the physical developer according to the present invention will be used merely as a scientific tool in light and electron microscopic applications, to better visualize particular substances, e.g. on histological coupes, on chromatograms, electrophoretograms, blots, etc. It is found that the present physical developer is especially useful for the immunological detection of antigens both in cell and tissue sections and in whole mount (intact cell) specimens. The achieved sensitivities are very high and the resulting labelling pattern is more homogeneous than with art-known physical developers, especially when ultra small markers are applied, such as colloidal gold particles of about 1 to 3 nm. Apart from its scientific utility, the physical developer according to the present invention will find utility in a wide variety of diagnostic tests such as, for example, the following: the detection and characterisation of subpopulations of T-lymphocytes; pregnancy tests based on the presence of certain hormones (chorionic gonadotropin) in the urine, diagnostic tests for various infectious diseases of fungal or bacterial origin, e.g. gonorrhoea, and in particular of for diseases of viral origin, such as, for example, hepatitis B, rubella, poliomyelitis and the like, auto-immune-diseases e.g. Lupus erythematosus and immune deficiency diseases, e.g. AIDS; diagnostics for metabolic, endocrinological and various endogenous diseases, including diagnostics for the detection of congenital malfunctions of embryos based on the presence of specific proteins in the amnion fluid.

Hence it can be employed in virtually all circumstances for which immunological techniques are conceived at present. In addition the physical developer according to the present invention may also be employed in the determination and/or detection of acceptor substances, such as proteins or nucleic acids, which are directly immobilized in or on a solid support and bound with a colloidal marker following procedures described in the European Patent Publication No. 0,165,633 and Analytical Biochemistry 145, 315–321

(1985). Said method comprises the subsequent steps of contacting a protein or nucleic acid support for a given time, with a sufficient concentration of colloidal markers suspended in a medium, preferably containing a detergent that does not interfere with protein or nucleic acid binding, like for example 0.1% of the non-ionic detergent Tween 20, and appropriately pH adjusted, and adding a physical developer whereby during the reaction or after an adequate reaction time the formed metal particles are quantitatively and/or qualitatively determined. The physical developer according to this invention improves the sensitivity of this method without the drawbacks associated with the traditional developers.

The method according to the invention offer a framework which can be used for a wide variety of routine and experimental applications. Due to their nature and ease of handling, the methods lend themselves particularly for simple and rapid qualitative or semi-quantitative assays. These can be oriented towards use by experienced laboratory technicians as well as by non-technically trained medical trained personnel or laymen. The methods can also be easily automated which is an important factor when large numbers of identical determinations must be carried out, e.g., in blood banks and specialized clinical laboratories.

In further aspect of the invention there are provided products for depositing silver particles on a marker which catalyzes the reduction of silver ions from a physical developer. Said products comprise some or all of the ingredients required to conduct assay methods as described hereinabove. Said products can be presented in a commercially packaged form, e.g. as a composition or admixture when the ingredients are compatible, in a test device configuration, or as a test-kit, i.e. a packaged combination of two or more containers holding the necessary ingredients. In its simplest configuration said product consists of a physical developer solution as described hereinbefore. Preferably said products are presented as test kits comprising an enhancer solution and an initiator solution which upon mixing of two equal volumes of each solution yield a light-stable physical developer as described hereinbefore. Said test-kits may further comprise ingredients appropriate for specific assay methods such as specific binding agents labelled with metal markers which catalyze the reduction of silver ions from the physical developer, non-labelled binding agents specific to analytes together with labelled binding agents specific to said non-labelled binding agents. Obviously, the present products may also include other useful reagents such as buffers, diluents, standards and the like.

EXAMPLES

Example 1

Materials and methods 1.1. Preparation of a protected physical developer I

Two liquid components of this developer were prepared separately. Solution A was made by dissolving b 17.85 g citric acid, 7.05 g sodium citrate, 40 g imidazole and 1.86 g silver nitrate into 500 ml water. Solution B consists of 32.9 g sodium citrate, 10 g sodium sulphite, 0.6 g N-(p-hydroxyphenyl)glycine and 15.32 g citric acid into 1000 ml water.

1.2 Preparation of a protected developer II

Two liquid components of this developer were prepared separately. Solution A was made by dissolving 17.85 g citric acid, 7.05 g sodium citrate, 40 g imidazole, 1.86 g silver nitrate and 0.25 g Pinakryptol Yellow ® dissolved into about 5 ml of N,N-dimethyl-formamide. The solution was diluted with water to 500 ml. Solution B consists of 32.9 g sodium citrate, 10 g sodium sulphite, 0.6 g N-(p-hydroxyphenyl) glycine and 15.32 g citric acid into 1000 ml water.

1.3. Method for measuring selfnucleation

The reagents are brought to 20° C. by putting them in a thermostated waterbath at 20° C. 1 ml of solution A and 1 ml of solution B are mixed in a plastic cuvette and put in a spectrophotometer thermostated at 20° C. The increase in the optical density at 500 nm is monitored and registered continuously.

1.4. Visual inspection of selfnucleation

A visual control test for silver nucleation is carried out by mixing 1 ml of solution A and 1 ml of solution B in a transparent polystyrene test tubel The time is registered when the first turbidity is seen. This test can be done in the dark and in the light conditions.

Results

1. Measuring selfnucleation

The test for measuring the selfnucleation was executed using the test described in 1.3 using the protected physical developer I and II described in 1.1 and 1.2. This test shows the selfnucleation time in absence of light. The results are shown in table 1 and 2. As shown, there is no difference in the selfnucleation in the dark, using the protected physical developer I and II.

TABLE 1

| self-nucleation in dark for physical developer I | |
|---|---|
| Times (minutes) | Optical density at 500 nm |
| 0 | 0.000 |
| 2 | 0.000 |
| 4 | 0.001 |
| 6 | 0.001 |
| 8 | 0.001 |
| 10 | 0.000 |
| 12 | 0.000 |
| 14 | 0.000 |
| 16 | 0.000 |
| 18 | 0.000 |
| 20 | 0.000 |

TABLE 2

| self-nucleation in dark for physical developer II | |
|---|---|
| Times (minutes) | Optical density at 500 nm |
| 0 | 0.000 |
| 2 | 0.000 |
| 4 | 0.000 |
| 6 | 0.000 |
| 8 | 0.000 |
| 10 | 0.000 |
| 12 | 0.000 |
| 14 | 0.000 |
| 16 | 0.000 |
| 18 | 0.000 |
| 20 | 0.000 |

2. Visual inspection of selfnucleation

The test for visual control of the selfnucleation was executed using the test described in 1.4 using the protected physical developers I and II described in 1.1 and 1.2. The results of this test is summarized in table 3.

TABLE 3

|  | physical developer I | physical developer II |
|---|---|---|
| First selfnucleation in full light | 6 minutes | 27 minutes |
| First selfnucleation in dark | >120 minutes | >120 minutes |

We claim:

1. A physical developer comprising an aqueous solution of silver ions, a densensitizing agent and a reducing agent.

2. A physical developer according to claim 1 wherein the desensitizing agent is 6-ethoxy-1-methyl-2-(3-nitrostyryl)quinolinium methyl sulfonate.

3. A physical developer according to claim 1 comprising a molar excess of complexant with respect to the silver ions.

4. A physical developer according to claim 3 wherein the complexant is histidine, imidazole, benzimidazole, pyrazole, pyridine, aminopyridine, nicotinamide, quinoline or purine.

5. A physical developer according to claim 1 wherein the reducing agent is 1,2-dihydroxybenzene, 1,4-dihydroxbenzene, 4-methylaminophenolsulfate, 4-aminophenol, 1,4-diaminobenzene, 1,2-diaminobenzene, N-(4-hydroxyphenyl)glycine, 2,4-diaminophenol, 1-phenyl-3-hydroxypyrazole or a mixture thereof.

6. A physical developer according to claim 1 obtained by mixing
   a) an aqueous solution comprising a reducing agent and optionally a buffer system and one or more adjuvants; and
   b) an aqueous solution comprising silver ions, a densensitizing agent, a molar excess of complexant with respect to the silver ions and optionally a buffer system and one or more adjuvants.

* * * * *